United States Patent [19]
Birkenmeyer et al.

[11] Patent Number: 5,453,355
[45] Date of Patent: Sep. 26, 1995

[54] **OLIGONUCLEOTIDES AND METHODS FOR THE DETECTION OF *NEISSERIA GONORRHOEAE***

[75] Inventors: Larry G. Birkenmeyer, Chicago; Shanfun Ching, Libertyville; Yoshihiro Ohhashi, Gurnee; Janet K. Winkler, Lindenhurst, all of Ill.

[73] Assignee: Abbott Laboratories, Abbott Park, Ill.

[21] Appl. No.: 116,388

[22] Filed: Sep. 3, 1993

Related U.S. Application Data

[63] Continuation-in-part of Ser. No. 722,798, Jun. 28, 1991, which is a continuation-in-part of Ser. No. 470,674, Jan. 26, 1990, abandoned.

[51] Int. Cl.$^6$ .............................. C12Q 1/68; C12P 19/34; C07H 21/04
[52] U.S. Cl. .......................... 435/6; 435/91.2; 536/24.32; 536/24.33; 935/78
[58] Field of Search .................. 435/91.2, 6; 536/24.32, 536/24.33; 935/78

[56] References Cited

U.S. PATENT DOCUMENTS

| | | | |
|---|---|---|---|
| 4,965,188 | 10/1990 | Mullis et al. | 435/6 |
| 5,162,199 | 11/1992 | Stern et al. | 435/6 |

FOREIGN PATENT DOCUMENTS

| | | |
|---|---|---|
| 0382433A2 | 8/1990 | European Pat. Off. . |
| 0404161A2 | 12/1990 | European Pat. Off. . |
| WO92/13871 | 8/1992 | WIPO . |
| WO93/00447 | 1/1993 | WIPO . |

OTHER PUBLICATIONS

Preliminary Evaluation of the Ligase Chain Reaction for Specific Detection of *Neisseria gonorrhoeae* Birkenmeyer, et al *Journal of Clinical Microbiology*, pp. 3089–3094, 1992.
Silent pilin genes of *Neisseria gonorrhoeae* MS11 and the occurrence of related hypervariant sequences among other gonococcal isolates Haas, et al *Molecular Microbiology*, vol. 6, No. 2, pp. 197–208, 1992.
L-pilin variants of *Neisseria gonorrhoeae* MS11 Manning, et al *Molecular Microbiology*, vol. 5, No. 4, pp. 917–926, 1991.
Structural analysis of the pilE region of *Neisseria gonorrhoeae* P9 Perry, et al *Gene*, vol. 60, pp. 85–92, 1987.
Meyer et al., *PNAS* 81, 6110–6114 (1984).

*Primary Examiner*—Margaret Parr
*Assistant Examiner*—Kenneth R. Horlick
*Attorney, Agent, or Firm*—Thomas D. Brainard; Paul D. Yasger

[57] ABSTRACT

The present invention relates to oligonucleotide probes and primers useful in detecting *Neisseria gonorrhoeae* e.g. by the polymerase chain reaction. The present invention is also directed to methods for detecting *Neisseria gonorrhoeae* by the polymerase chain reaction. The probes and primers are specific for the pilin gene.

14 Claims, 3 Drawing Sheets

```
1'       1(+)    5'    CCAGCTGAGG CAAATTAGG-3'
1        3(+)    5'    CCAAATGAGG CAAATTAGG-3'
A        4(+)                                                                                 5'-AT->
IP       8(+)                                                                                 5'-GAT->

Pos. No.         827         847         867         887
9(+)    CCAAATGAGG CAAATTAGGC CTTAAATTTT AAATAAATCA AGCGGTAAGT GATTTTCCAC CCGCCCGGAT
9(-)    GGTTTACTCC GTTTAATCCG GAATTTAAAA TTTATTTAGT TCTCCATTCA GTAAAAGGTG GGCGGGCCTA

A2       6(+)    5'-CGGGC GGCTTGTTC-3'
A        4(+)con                                                                              5'-CGGGC GGCTTGTTC-3'
IP       8(+)con                                                   5'-CGGGC GGCTTGTCTT TTAAGGGGTTT GCAAGGCGGG-3'

Pos. No.         907         927         947         967
9(+)con  CAACCCGGGC GGCTTGTCTT TTAAGGGTTT GCAAGGCGGG CGGGGTCGTC CGTTCCGGTG GAAATAAATAT ATCGAT
9(-)con  GTTGGGCCCG CCGAACAGAA AATTCCCAAA CGAACCGCCC GCCCCAGCAG GCAAGGCCAC CTTTATTATA TAGCTA B2       7(-)                                                                3'-CCC GCCCCAGCA-5'
B        5(-)                                                                3'-CCC GCCCCAGCAG GCAAG-5'
2        2(-)                                                                                3'-GGCCAC CTTTATTATA TAGCTA-5'
```

FIG.1

OLIGONUCLEOTIDES AND METHODS FOR THE DETECTION OF *NEISSERIA GONORRHOEAE*

This application is a continuation-in-part of U.S. Ser. No. 07/722,798, filed Jun. 28, 1991 (pending), which is a continuation-in-part of U.S. Ser. No. 07/470,674, filed Jan. 26, 1990 (now abandoned), and which is related to U.S. Ser. No. 07/634,771, filed Jan. 9, 1991 (pending).

FIELD OF THE INVENTION

The invention relates to oligonucleotides and compositions of oligonucleotides as primers and as oligonucleotide "label" probes useful in detecting *N. gonorrhoeae*. The invention also relates to methods, e.g., by the polymerase chain reaction (PCR), for the detection of *N. gonorrhoeae*.

BACKGROUND OF THE INVENTION

*Neisseria gonorrhoeae* (gonococci) is the etiologic agent of gonorrhea, an important sexually transmitted disease found throughout the world. In males, the infection is easily diagnosed and treated. However, less than 25% of females with gonorrhea have a readily discernable endocervical infection. As many as 10 to 15 percent of infected women develop gonococcal pelvic inflammatory disease which can result in damage to the fallopian tubes. Subsequently, gonococci may ascend to the ovaries and into the peritoneal cavity which may lead to sterility and which in some cases can be life threatening. The disease if left untreated in either males or females can also cause gonococcal arthritis.

Traditionally, diagnosis of gonorrhea is accomplished by culturing the organism from a clinical specimen suspected of harboring *N. gonorrhoeae*. Culture techniques include procedures described in, Criteria And Techniques For The Diagnosis Of Gonorrhea, published by the Center for Disease Control, Atlanta, Ga. These culture techniques are laborious and time consuming requiring a minimum of 24 hours of culturing and result in presumptive identification of *N. gonorrhoeae*. Confirmation of the identification is typically accomplished by sugar fermentation patterns, fluorescent antibody staining, or agglutination assays.

In order to improve the efficiency and accuracy of the detection of *N. gonorrhoeae*, alternative methods such as enzyme immunoassay have been developed. (Grubin, L., and Osborne, N. G., Obstet. Gynecol. 69:350–353 (1987)). DNA hybridization assays have also been described for the detection of *N. gonorrhoeae*. (U.S. Pat. No. 4,900,659 by Lo; Pauke, E. S., et al., J. Clin. Microbiol. 29:883–888 (1991); Torres, M. J., et al. Mol. Cell. Probes 5:49–54 (1991); Totten, P. A., et al., J. Infect. Dis. 148:462–471 (1983); and Perfin, et al., J. Infect. Dis. 152:59 (1986)).

U.S. Pat. No. 5,162,199 to Stem and Wolff addresses the use of DNA probes for the detection of *N. gonorrhoeae* and *N. meningitidis* using hybridization assays such as slot blots and southern blots. The probes were derived from the PHI, Pil I, Iga2, Iga1, Opa1, Opa2, and Opa3 genes which code for various Neisseria specific proteins.

In selecting DNA probe sequences for the detection of *N. gonorrhoeae*, it is important to recognize that *N. gonorrhoeae* and *N. meningitidis* exhibit up to about 93% chromosomal DNA homology (Hoke and Vedros, Int. J. Syst. Bacter. 32:57–66 (1982)). Thus, in order to develop effective materials and methods for the diagnosis of *N. gonorrhoeae* it is important to select nucleotide sequences that are specific for *N. gonorrhoeae* and which exhibit no cross reactivity with other Neisseria species or other bacteria. The sequence known as pil E has been described by Meyer, T. F., et al., Proc. Natl. Acad. Sci. U.S.4.81:6110–6114 (1984). The pil E gene codes for a predominant surface antigen of *N. gonorrhoeae* which allows adhesion of the bacterium to various host cells. Pil E expression in the MS 11 strain of *N. gonorrhoeae* is controlled by at least two and possibly three genetic loci dispersed over a large region of the *N. gonorrhoeae* chromosome.

Also of interest to the background of the present invention is a technique useful in amplifying and detecting target DNAs known as the polymerase chain reaction. The polymerase chain reaction provides a method for selectively increasing the concentration of a target DNA having a particular sequence. Details of the polymerase chain reaction are provided by Mullis, K. et al. U.S. Pat. No. 4,683,202; Erlich, H., U.S. Pat. No. 4,582,788; Saiki et al., U.S. Pat. No. 4,683,195; Mullis, K. B., Cold Spring Harbor Symp. Quant. Biol 51:263–273 (1986); Saiki, R. K. et al., Bio/Technology 3:1008–1012 (1985); and Mullis, K. B., et al. Meth. Enzymol. 155:335–350 (1987), all of which are incorporated herein by reference.

Despite the aforementioned methods, there remains a need for a rapid, sensitive, specific and reproducible method for the detection of *Neisseria gonorrhoeae*.

SUMMARY OF THE INVENTION

The present invention is directed to oligonucleotide probes useful for detecting target DNA from *N. gonorrhoeae*. Such an oligonucleotide probe is from 12 to about 50 nucleotides long and possesses sufficient complementarity or homology to the sequences shown in SEQ ID NOS. 1, 2, 3, 5 or 8 to hybridize with such sequence or its complement under hybridizing conditions, as defined herein. Sufficient complementarity or homology generally requires about 80% to 100% complementarity or homology. Shorter probes typically require higher percentage ranges, while longer probes typically are useful with lower percentage ranges. Preferred are probes in the range of 15 to 40, usually about 20–25 nucleotides in length.

The present invention is also directed to compositions useful in PCR for detecting target DNA from *N. gonorrhoeae*, said compositions comprising pairs of oligonucleotides selected from: primer set 1 (SEQ ID NOS. 2 and 3), primer set 2 (SEQ ID NOS. 3 and 5), primer set 3 (SEQ ID NOS. 3 and 7), primer set 4 (SEQ ID NOS. 4 and 2), primer set 5 (SEQ ID NOS. 4 and 5), primer set 6 (SEQ ID NOS. 4 and 7), primer set 7 (SEQ ID NOS. 6 and 2), primer set 8 (SEQ ID NOS. 6 and 5), primer set 9 (SEQ ID NOS. 6 and 7), primer set 10 (SEQ ID NOS. 1 and 2), primer set 11 (SEQ ID NOS. 1 and 5), primer set 12 (SEQ ID NOS. 1 and 7), and primer set 13 (SEQ ID NOS. 10 and 13) as defined herein and combinations thereof. PCR compositions include primers that are sufficiently homologous with the above mentioned primers to hybridize with the complements of the named primers under hybridizing conditions, as defined herein.

Combinations of primers or primer sets may comprise "nested primers" in which primary primers are used to amplify the target DNA after which secondary or "nested primers" are used to amplify the amplification products produced during the first amplification series. Nested primers are described in EP-A-357 011 and elsewhere in the literature.

In another of its aspects, the present invention is directed to methods for detecting target DNA from N. gonorrhoeae using the polymerase chain reaction. These methods generally involve providing a sample suspected of containing the target DNA, providing a DNA polymerase, four deoxynucleotide triphosphates and a primer set selected from the group consisting of primer set 1 (SEQ ID NOS. 2 and 3), primer set 2 (SEQ ID NOS. 3 and 5), primer set 3 (SEQ ID NOS. 3 and 7), primer set 4 (SEQ ID NOS. 4 and 2), primer set 5 (SEQ ID NOS. 4 and 5), primer set 6 (SEQ ID NOS. 4 and 7), primer set 7 (SEQ ID NOS. 6 and 2), primer set 8 (SEQ ID NOS. 6 and 5), primer set 9 (SEQ ID NOS. 6 and 7), primer set 10 (SEQ ID NOS. 1 and2), primer set 11 (SEQ ID NOS. 1 and 5), primer set 12 (SEQ ID NOS. 1 and 7), and primer set 13 (SEQ ID NOS. 10 and 13) and combinations thereof. The following cycle is then repeated at least once: denaturation; hybridizing the oligonucleotide primer set to the target DNA; extending said primers in the 5' to 3' direction in a template-dependant manner thereby providing an amplification product; and detecting the amplification products. Preferably, the cycle preceding detection is repeated from about 10 to about 50 times.

Still other aspects of the present invention include the use of oligonucleotides of the present invention for detecting target DNA from N. gonorrhoeae using nucleic acid hybridization assays including but not limited to slot blot, Southern blots, dot blots and sandwich immunocapture assays.

Selected oligonucleotides of the present invention are also useful in detecting target DNA from N. gonorrhoeae using the ligase chain reaction.

Additional aspects of the invention include kits useful for detecting target DNA from N. gonorrhoeae. The kits comprise one or more suitable containers containing one or more primer sets, a polymerase reagent, and one or more deoxynucleotide triphosphates and an internal probe such as (SEQ ID NO. 8).

BRIEF DESCRIPTION OF THE FIGURES

FIG. 1 depicts the DNA sequence for a 146 base pair region (SEQ ID NO. 9) of the pil E gene (also referred to herein as Pilin-2) described by Meyer, T. F., et al., (position 827–972) along with the primers and probes of this application. The double stranded DNA target is shown in the boxes; primers and probes homologous with the sense strand (+) are shown above the target, while primers and probes homologous with the antisense strand (−) are shown below the target. This figure shows how the primers align, where they overlap and to which strand they are homologous. The target (SEQ ID NO. 9) and probe A and Internal Probe (IP) (SEQ ID NOS. 4 and 8) wrap around from the top target box to the bottom. The underlined bases in Primer 1' represent deliberate mismatches.

DETAILED DESCRIPTION OF THE INVENTION

Figure 2:
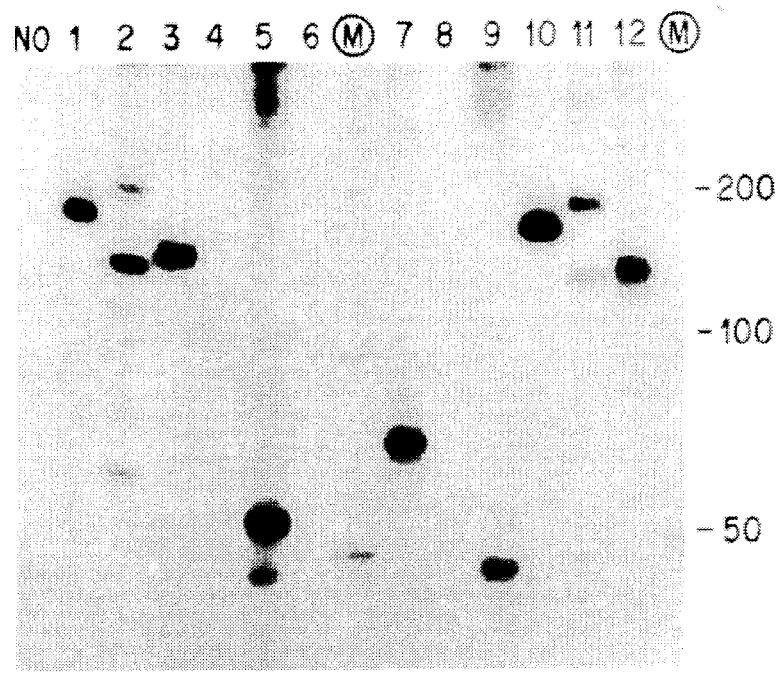
FIG. 2 represents a photograph of an autoradiograph of a hybridization analysis of PCR products produced using primer sets 1–12 and target DNA from N. gonorrhoeae. See Example 1.

The present invention is directed to oligonucleotides useful in the detection of Neisseria gonorrhoeae (e.g. SEQ ID NOS. 1–8 and 10–13). Illustrative oligonucleotide probes are set forth in Table 1, below, wherein the map position and the SEQ ID NO of each probe is indicated. The "STRAND" column indicates whether the primer is homologous with the sense (+) or antisense (−) strand of the target DNA.

TABLE 1

Oligonucleotides Derived From The N. gonorrhoeae pil E Gene

| | Map Location | SEQUENCE | STRAND | SEQ ID NO. |
|---|---|---|---|---|
| Pn 1 | 827–845 | 5'-CCAAATGAGGCAAATTAGG-3' | (+) | (SEQ ID NO. 3) |
| Pn 2 | 972–951 | 5'-ATCGATATATTATTTCCACCGG-3' | (−) | (SEQ ID NO. 2) |
| Pn 1' | 827–845 | 5'-CCAGCTGAGGCAAATTAGG-3' | (+) | (SEQ ID NO. 1) |
| Pn A | 895–914 | 5'-ATCAACCCGGGCGGCTTGTC-3' | (+) | (SEQ ID NO. 4) |
| Pn A$_2$ | 902–914 | 5'-CGGGCGGCTTGTC-3' | (+) | (SEQ ID NO. 6) |
| Pn B | 951–934 | 5'-GAACGGACGACCCCGCCC-3' | (−) | (SEQ ID NO. 5) |
| Pn B$_2$ | 945–934 | 5'-ACGACCCCGCCC-3' | (−) | (SEQ ID NO. 7) |
| Internal Probe (IP) | | | | |
| | 894-936 | 5'-GATCAACCCGGGCGGCTTGTCTTTTAAGGGTTTGCAAGGCGGG-3' | (+) | (SEQ ID NO. 8) |

Seven oligonucleotides (SEQ ID NOS. 1–7) were selected principally as primers for the polymerase chain reaction (PCR) detection of N. gonorrhoeae. Table 1 also shows an internal probe (SEQ ID NO. 8) useful for detecting PCR products produced by the PCR method of the present invention.

Each of the primers comprise deoxyribonucleic acid (DNA) and may be routinely synthesized using conventional phosphoramidite or other chemistry and the instruments available from Applied Biosystems, Inc., (Foster City, Calif.), DuPont (Wilmington, Del.) or Milligen, (Bedford, Mass.). Natural-source primers may also be used, as may primers bearing ribonucleotide residues.

Compositions of the present invention useful in the PCR for detecting target DNA from N. gonorrhoeae include: primer set 1 (SEQ ID NOS. 2 and 3); primer set 2 (SEQ ID NO. 3 and 5); primer set 3 (SEQ ID NOS. 3 and 7); primer set 4 (SEQ ID NOS. 4 and 2); primer set 5 (SEQ ID NOS. 4 and 5); and primer set 6 (SEQ ID NOS. 4 and 7); primer set 7 (SEQ ID NOS. 6 and 2); primer set 8 (SEQ ID NOS. 6 and 5); primer set 9 (SEQ ID NOS. 6 and 7); primer set 10 (SEQ ID NOS. 1 and 2); primer set 11 (SEQ ID NOS. 1 and 5); primer set 12 (SEQ ID NOS. 1 and 7); and primer set 13 (SEQ ID NOS. 10 and 13). These compositions are further identified in Table 2 in Example 1, infra.

The invention is also directed to a method for detecting *N. gonorrhoeae* using the polymerase chain reaction (PCR) in conjunction with the compositions of the present invention. In general, PCR involves hybridizing oligonucleotide primers to each strand of a denatured double-stranded target DNA in a sample, extending each primer in a template-dependent manner using a polymerase reagent, treating the sample under denaturing conditions to separate the primer extension products from their templates and repeating the process at least once. In the practice of the present invention, it is preferred that the process be repeated from about 10 to about 50 times. Details of the polymerase chain reaction are provided by Mullis, K. et al. U.S. Pat. No. 4,683,202; Efiich, H., U.S. Pat. No. 4,582,788; Saiki et al., U.S. Pat. No. 4,683,195; Mullis, K. B., Cold Spring Harbor Symp. Quant. Biol 51:263–273 (1986); Saiki, R. K. et al., Bio/Technology 3:1008–1012 (1985); and Mullis, K. B., et al. Meth. Enzymol. 155:335–350 (1987), all of which are incorporated herein by reference.

Preferred in the practice of the present methods is a thermostable DNA polymerase such as the Taq polymerase; although, other DNA polymerases such as the Klenow fragment of DNA polymerase I may be used. A thermostable polymerase is preferred because it is capable of withstanding the temperatures necessary to denature the target DNA and to denature primer extension products. Thus, the use of heat stable DNA polymerases obviates the need to add additional DNA polymerases after every denaturation step of the PCR cycle. Several heat stable polymerases are commercially available from, for example, Molecular Biology Resources (MBR, Milwaukee, Wisc.), Promega (Madison, Wisc.) and others.

It should be noted that probes and primers useful in the practice of the present invention also include probes and primers substantially homologous to those set forth in Table 1. Substantially homologous probes/primers are those that are sufficiently complementary to their respective target strands to hybridize therewith under hybridizing conditions. For example, substitutions may be made in the base sequence, so long as the oligonucleotide retains sufficient complementarily to the target DNA to hybridize therewith especially at or near the 3' end of the primer. Also, non-complementary nucleotide fragments may be attached to the 5' end of the oligonucleotide primer with the remainder of the primer remaining complementary to the target sequence. When utilizing oligonucleotide primers that do not match the target strand perfectly (substantially homologous primers), hybridization conditions may be altered to insure hybridization to the target, although specificity may suffer somewhat under lower stringency.

"Hybridization" or "hybridizing" conditions is defined generally as stringency conditions which promote nucleation and annealing. It is well known in the art, however, that such annealing is dependent in a rather predictable manner on several parameters, including temperature, ionic strength, probe length and G:C content of the probes. For example, lowering the temperature of the reaction promotes annealing. For any given set of probes or primers, melt temperature, or Tm, can be estimated by any of several known methods. Typically, diagnostic applications utilize hybridization temperatures which are slightly below the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased probe/primer length are also known to stabilize duplex formation because G:C pairings involve 3 hydrogen bonds where A:T pairs have just two, and because longer probes/primers have more hydrogen bonds holding the duplex together. Thus a high G:C content and longer probe/primer lengths impact the "hybridization conditions" by elevating the melt temperature.

Once probes or primers are selected for a given diagnostic application, the G:C content and length will be known and can be accounted for in determining precisely what "hybridization conditions" will encompass. Since ionic strength is typically optimized for enzymatic activity, the only parameter left to vary is the temperature. For improved specificity, the hybridization temperature is selected slightly below the Tm of the probe/primer; typically 2°–10° C. below the Tm. Thus, obtaining suitable "hybridization conditions" for a particular probe or primer set and system is well within ordinary skill of one practicing this art.

Various methods may then be employed for detection of amplification products. For example, aliquots of the PCR reactions may be analyzed by agarose gel electrophoresis and staining with ethidium bromide as described in Sambrook et al., Molecular Cloning: A Laboratory Manual, Cold Spring Harbor Press (1989). Amplification products appear as a fluorescent band in the gel when exposed to ultraviolet light.

Other methods for the detection of amplification products include hybridization, especially solution hybridization, using a labeled, internal oligonucleotide probe complementary to a region of DNA lying between the oligonucleotide primers used for amplification. Any DNA sequence found between each primer of a primer pair may be suitable for use as an internal probe for the detection of amplification products. Preferably the internal probe is from about 10 to about 150 bases in length. The internal probe may be labelled with $^{32}$P, biotin or any other label capable of generating a signal. In the present embodiment, the internal probe is 43 bases in length and corresponds to nucleotides 892–937 of the Pilin-2 gene (SEQ ID NO. 8). Labeling of the internal probe $^{32}$P may be accomplished by a number of methods well known to those skilled in the art. For example, 5'-end labeling of the internal probe may be accomplished by either a forward reaction or an exchange reaction using the enzyme polynucleotide kinase. In the forward reaction T4 polynucleotide kinase is used, adding $^{32}$p from [$^{32}$P]ATP to the 5' end of the internal probe which has been dephosphorylated with alkaline phosphatase, using standard techniques which are described in detail Sambrook, J. et al., Molecular Cloning: A Laboratory Manual, Cold Spring Harbor Laboratory Press (1989). In the exchange reaction an excess of ADP (adenosine diphosphate) is used to drive an exchange of a 5'-terminal phosphate from the internal probe to ADP which is followed by the transfer of $^{32}$P from $\alpha^{32}$P-ATP to the 5'-end of the oligonucleotide. This reaction is also catalyzed by T4 polynucleotide kinase.

Other methods of labeling DNA for use as internal probes are the nick translation method, Sambrook, J. et al, Molecular Cloning: A Laboratory Manual. Cold Spring Harbor Laboratory Press (1989), and the random priming method (RPL), (Feinberg, A. P. and Vogelstein, B. Anal. Biochem. 132:6–13 [1984], Feinberg, A. P. and Vogelstein, B., Anal. Biochem. 137:266–267 [1984]). The nick translation method involves nicking of the template DNA under carefully controlled conditions using DNAase I. DNA polymerase I is then added to the nicked DNA to facilitate the addition of nucleotides at the 3' end and removal of nucleotides at the 5' end of a nick. This process replaces preexisting nucleotides with labelled nucleotides. The main disadvantages of this labeling system are that the balance between synthesis and removal of nucleotides from the 5' end needs to be timed perfectly in order to achieve synthesis and avoid degradation.

The random primer labeling (RPL) method of labeling utilizes synthetic oligonucleotides primers six to nine bases long (synthesized in all possible base combinations) to hybridize to denatured DNA. The hybridized primers serve to prime DNA synthesis by either the Klenow fragment of DNA polymerase I or T7 DNA polymerase. (Feinberg, A. P. and Vogelstein, B. Anal. Blochem. 132:6–13 (1984), Feinberg, A. P. and Vogelstein, B., Anal. Blochem. 137:266–267 (1984)).

Synthetic primers and probes can also be labeled by the incorporation during synthesis of labeled phoshoramidite reagents.

Another detection method for the amplification and detection of target DNA is sandwich immunocapture, described in EP 357 011 which is incorporated herein by reference. This method involves amplification employing 5' haptenated primers directed to the target DNA and sandwich-like immunodetection of the double-stranded amplification products. More specifically, the method involves hybridizing to each of the target strand and its complementary strand respective oligonucleotide primers, one of which is conjugated to a member of a reactive pair, and the other which is conjugated to or capable of reacting with a detectable moiety, typically being conjugated to a different hapten. These primers are then used in a typical PCR type reaction of denaturation hybridization and extension for one or more cycles with a resulting double stranded product which can be captured on a solid phase having the other member of the first reactive pair so that the double stranded products become linked to the solid phase by virtue of the interaction of the first reactive pair. The second reactive pair can be used to attach a labeled conjugate to the solid phase via the amplification product "sandwich".

In a variation on this sandwich method, one haptenated primer is employed, while an internal hybridization probe is used for the other part of the sandwich. The internal probe may be immobilized and the hapten is detected, or vice versa.

In addition, EP 357 011 describes the use of nested primers in a PCR type amplification method. The nested primer method involves denaturing a double stranded target sequence and annealing "primary primers" to the single strands in the target region of interest. Using PCR, primary extension products are synthesized. This sequence of steps is then repeated to a desired degree of amplification. Secondary primers are then annealed to the primary extension products and PCR is performed as above. The secondary primers are synthesized so as to hybridize to regions on their respective strands near or adjacent to, (but not overlapping) where the 3' terminus of the primary primers would be hybridized to the same strands. The advantage to using primary and secondary nested primers is improved specificity in that secondary extension products will not be synthesized unless the secondary primers hybridize to the primary extension products. Other embodiments of the method are also described including a method wherein only a single nested secondary primer is used.

Many combinations of nested primers are useful in the practice of the present invention. The table below lists by SEQ ID No. illustrative, but not exhaustive, combinations of nested primers having two outside or primary primers and one or two inside or secondary primers. In the three primer system (single nested primer) one of the original outside primers is also used as a secondary primer.

| (+) Primary primer | (−) Primary Primer | (+) Secondary Primer | (−) Secondary Primer |
|---|---|---|---|
| 1 | 2 | 4 | 5 or 7 |
| 1 | 2 | 6 | 5 or 7 |
| 3 | 2 | 4 | 5 or 7 |
| 3 | 2 | 6 | 5 or 7 |
| 1 | 5 | 4 or 6 | 5 |
| 1 | 5 | 4 or 6 | 7 |
| 1 | 7 | 4 or 6 | 7 |
| 3 | 5 | 4 or 6 | 5 |
| 3 | 5 | 4 or 6 | 7 |
| 3 | 7 | 4 or 6 | 7 |
| 4 | 2 | 4 | 5 or 7 |
| 4 | 2 | 6 | 5 or 7 |
| 6 | 2 | 6 | 5 or 7 |

The invention will now be illustrated by way of the following non-limiting examples.

EXAMPLE 1

Detection of *N. Gonorrhoeae* Target DNA Using Pilin 2 Gene Derived Oligonucleotides The oligonucleotide primer sets listed in Table 2 were tested for their ability to detect target DNA from *N. gonorrhoeae* using the polymerase chain reaction.

TABLE 2

| Primer Set No. | Primers |
|---|---|
| 1 | Pn 1 (SEQ ID NO. 3) + Pn 2 (SEQ ID NO. 2) |
| 2 | Pn 1 (SEQ ID NO. 3) + Pn B (SEQ ID NO. 5) |
| 3 | Pn 1 (SEQ ID NO. 3) + Pn B2 (SEQ ID NO. 7) |
| 4 | Pn A (SEQ ID NO. 4) + Pn 2 (SEQ ID NO. 2) |
| 5 | Pn A (SEQ ID NO. 4) + Pn B (SEQ ID NO. 5) |
| 6 | Pn A (SEQ ID NO. 4) + Pn B2 (SEQ ID NO. 7) |
| 7 | Pn A2 (SEQ ID NO. 6) + Pn 2 (SEQ ID NO. 2) |
| 8 | Pn A2 (SEQ ID NO. 6) + Pn B (SEQ ID NO. 5) |
| 9 | Pn A2 (SEQ ID NO. 6) + Pn B2 (SEQ ID NO. 7) |
| 10 | Pn 1' (SEQ ID NO. 1) + Pn 2 (SEQ ID NO. 2) |
| 11 | Pn 1' (SEQ ID NO. 1) + Pn B (SEQ ID NO. 5) |
| 12 | Pn 1' (SEQ ID NO. 1) + Pn B2 (SEQ ID NO. 7) |
| 13 | 933.1 (SEQ ID NO. 10) + 933.4 (SEQ ID NO. 13) |

The PCR reaction mix contained final concentrations of IX Stoffel Buffer (10 mM KCl, 10 mM Tris-HCl) 6.25 µM $MgCl_2$, 1.25 µM each of dATP, dCTP, dGTP and dTYP, and $3 \times 10^{12}$ molecules of each primer in a total volume of 100 µl.

Prior to the addition of the Stoffel fragment of Taq polymerase all ingredients of the reaction were mixed and placed at 99° C. for 5 min. 10 units of the Stoffel fragment of Taq polymerase (AmpliTaq® DNA Polymerase, Stoffel Fragment, Perkin-Elmer Cetus, Norwalk Conn.) in Stoffel buffer was then added to the reaction mix. The complete reaction mix was then cycled in a Perkin-Elmer Model 480 Thermal Cycler as follows: melting at 94° C., 1 min.; annealing at 55° C., 1 min.; and extending at 72 ° C., 1 min. for total of thirty cycles followed by a single 9 min. extension at 72 ° C.

PCR amplification products were analyzed by solution hybridization as follows: 10% of each reaction mix was mixed with 1 μl of $^{32}$P-labelled (end-labelled) internal probe (SEQ ID NO. 8) as shown in Table 1. After the addition of $^{32}$P-labelled internal probe (SEQ ID NO. 8), the tubes were heated at 94° C. for 5 min. then placed directly onto wet ice for 10 min. Tracking dye (brom-phenol blue and xylene cyanol) was then added to the mixture and samples were loaded on an 8% native polyacrylamide gel for electrophoresis. Techniques for polyacrylamide gel electrophoresis are well known in the art and are described in Sambrook, J. et al., Molecular Cloning: A Laboratory Manual, Cold Spring Harbor Laboratory Press, Cold Spring Harbor, N.Y. (1989).

After electrophoresis, the gel was removed from its glass plate, rinsed, wrapped in plastic wrap, and autoradiographed on x-ray film in a light-tight container using two intensifying screens for 17 hours. Exposure time will vary with the specific activity of the probe, the amount of amplified product, with the quantity of probe used, and is easily determined by those of ordinary skill in the art.

FIG. 2 shows the results of this analysis. PCR primer sets 1 (lane 1 ), 2 (lane 2), 3(lane 3),5(lane5),7 (lane7),9(lane9), 10(lane 10), 11 (lane 11), and 12 (lane 12) each produced PCR products which hybridized to the internal probe. Primer sets 4, 6, and 8 (lanes 4, 6, and 8, respectively) each failed to produce products. Also, PCR reactions containing no target DNA gave no reaction products hybridizable to the internal probe. These results show that primers sets 1 (SEQ ID NOS. 2 and 3), 2 (SEQ ID NOS. 3 and 5), 3 (SEQ ID NOS. 3 and 7), 5 (SEQ ID NOS. 4 and 5), 7 (SEQ ID NOS. 6 and 12), 9 (SEQ ID NOS. 6 and 7), 10 (SEQ ID NOS. 1 and 2), 11 (SEQ ID NOS. 1 and 5), and 12 (SEQ ID NOS. 1 and 7) gave detectable signals and thus were capable of detecting the presence of target DNA from *N. gonnorhoeae* using the polymerase chain reaction. Primer set 13 was not included.

EXAMPLE 2

Cross-Reactivity of Primer Set 1 (SEQ ID NOS. 2–3) with DNA from Non-Neisseria Bacteria In order to examine the specificity of probe set 1 (SEQ ID NOS. 2 and 3) for *N. gonnorhoeae*, a series of PCR assays were performed as described in Example 1. Target DNAs were as follows: lane 1, *Proteus morganii* 5108, *E. coli* 3100, *E. coli* 8739, *Pseudomonas aeruginosa* 10145, *Enterobacter aerogenes* 13048; lane 2, *Acinetobacter calcoaceticus* JK, *Corynebacterium hoffmanni* JK, *Yersinia enterocolitica* 0193, *Alcaligenes faecalis* 0174, *Proteus vulgaris* A5113; lane 3, *Staphylococcus aureus* ROW, *Acinetobacter calcoaceticus* JK, *Acinetobacter calcoaceticus* 1217.21 JK, *Serratia marcesens* 4003, *Staphylococcus epidermidis* 3519; lane 4, *Bacillus subtilis* VV, *Klebsiella pneumoniae* 1 0013, *Salmonella enteritidis* ABB 155, *Providencia stuartii* 5313, *Enterobacter cloacae* 5047; lane 5, *Shigella sonnei, Mima polymorpha* v. oxidans, *Hemophilus influenzae* 123, *Hemophilus influenzae* 9334, *Herella vagincola*; lane 6, *Streptococcus pyogenes, Streptococcus faecalis, Lactobacillus plantarum, Salmonella minnesota, Hemophilus parainfluenza;* lane 7, *Aeromonas hydrophila, Corynebacterium* sp. 16–2, Corynebacterium sp. ICFA, Corynebacterium sp. E14, Veillonella sp. 131–6; lane 8, Veillonella sp. 131–9, *Moraxella osloensis, Trichomonas vaginalis* TV, *G. vaginalis* 14019, *Chlamydia trachomatis* 97032. Positive control samples containing 25 genome equivalents (lanes 12 and 13 ) and 100 genome equivalents (lanes 14 and 15) of *N. gonorrhoea* DNAs and negative controls containing only human placental DNA (lane 2) or no DNA (lane 1 ) were also included. Amplification products were assayed by solution hybridization, polyacrylamide gel, electrophoresis, and autoradiography as described in Example 1. Results are shown in FIG. 3.

Figure 3:
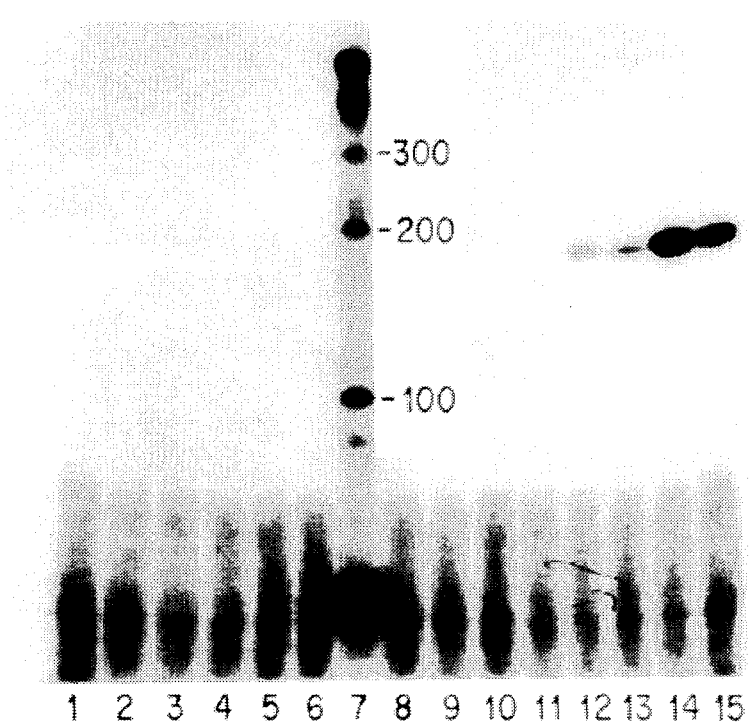
FIG. 3 represents a photograph of an autoradiograph of a hybridization analysis of the PCR products produced using primer set 1 and target DNA from a variety of bacterial sources. See Example 2.

As can be seen in FIG. 3, no amplification products were detected when target DNA from any of the 40 non-Neisseria bacteria were tested. However, a 146 bp *N. gonorrhoea* specific band was seen when target DNA from *N. gonorrhoeae* was used at 25 copies per reaction (lanes 12 and 13) and 100 copies per reaction (lanes 14 and 15). These data suggest that primer set 1 (SEQ ID NOS. 2–3) is specific for the detection of target DNA from *N. gonorrhoeae* in a polymerase chain reaction.

EXAMPLE 3

Cross-Reactivity of Primer Set 1 (SEQ ID NOS. 3–2) with DNA from Non-Gonococcal Species of Neisseria In order to examine the possible cross-reactivity of probe set 1 (SEQ ID NOS. 3 and 2) with DNA from non-gonococcal Neisseria species, assays were performed according to the procedures set forth in Example 1. Assays were performed using target DNA from *N. sicca, N. lactamica, N. meningitidis.* Control assays were also performed using 25 and 100 cell equivalents of *N. gonorrhoeae* target DNA, human placental target DNA and no target DNA. Amplification products were analyzed solution hybridization, polyacrylamide gel electrophoresis and autoradiography as described in Example 1.

Figure 4:
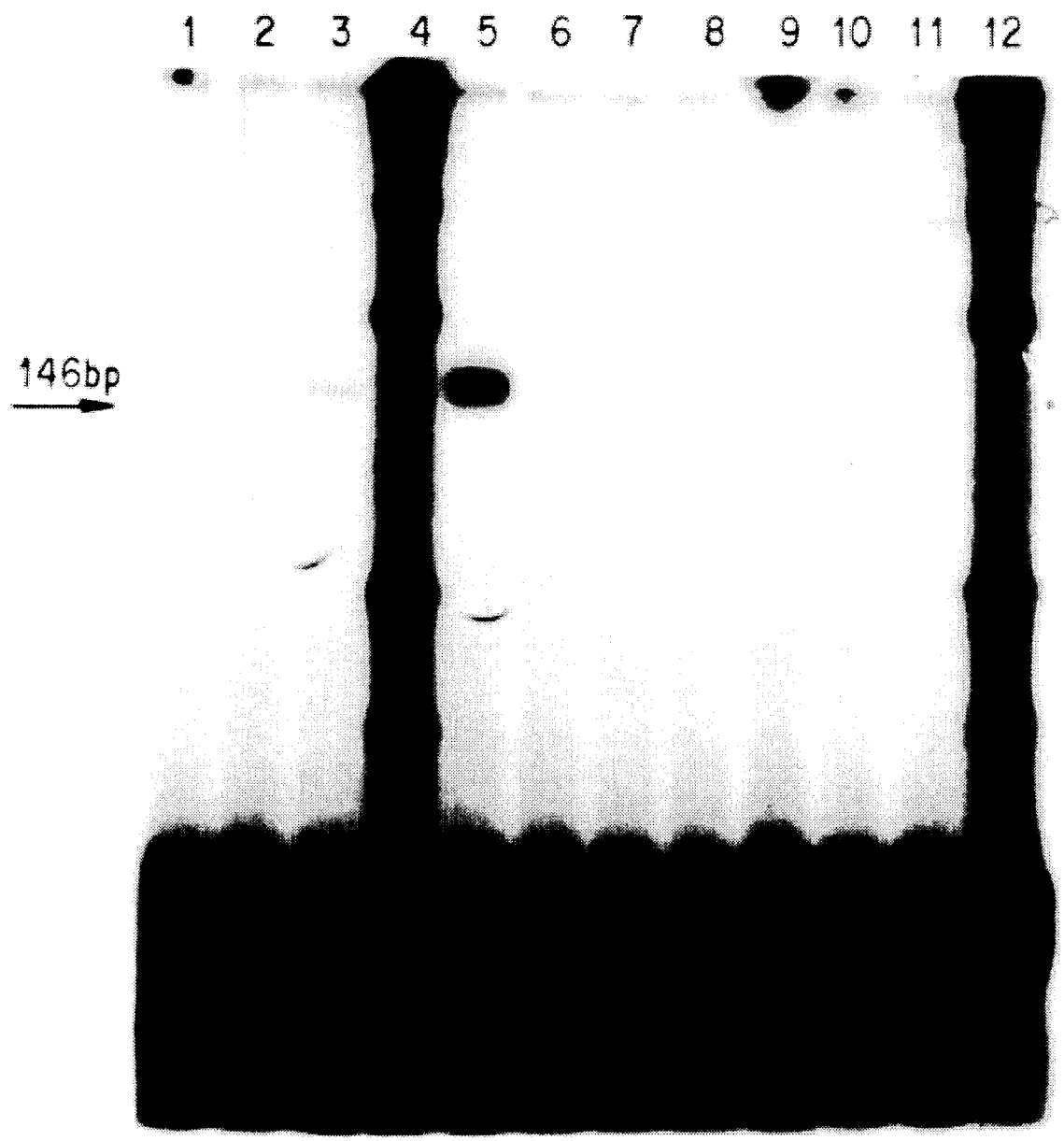
FIG. 4 represents a photograph of an autoradiograph of a hybridization analysis of PCR products obtained using primer set 1 and target DNA derived from N. gonnorhoeae, N. sicca, N. lactamica, and N. meningitidis. See Example 3.

As shown in FIG. 4, a 146 bp *N. gonorrhoeae* specific amplification product was seen only when the reaction contained 25 genome equivalents (lane 3) and 100 cell equivalents of *N. gonorrhoeae* target DNA. (lane 5). However, no amplification products were seen when target DNA was derived from *N. sicca* (lanes 6 and 7), *N. lactamica* (lanes 8 and 9), or *N. meningitidis* (lanes 10 and 11 ). In addition, no amplification products were seen when human placental DNA alone was in the reaction mixture (lane 2) or when no target DNA was present in the reaction mix (lane 1). These results indicate that probe set 1 (SEQ ID NOS. 2 and 3) exhibited no cross-reactivity with target DNA from other closely related species of Neisseria. Lanes 4 and 12 contain molecular weight markers.

EXAMPLE 4

Detection of N. gonorrhoeae Using Pilin-2 Derived Probes and the Ligase Chain Reaction Oligonucleotides derived from the Pilin-2 gene are also useful in detecting target DNA from N. gonorrhoeae using the ligase chain reaction (LCR). The ligase chain reaction is described in detail in EP-A-320 308 to Backman et al published Jun. 14, 1989, EP-A-439 182 to Backman et al. published Jul. 31, 1991, and in Birkenmeyer et al., J. Clin. Micro. 30: 3089–3094, (1992), all of which are incorporated herein by reference. By way of non-limiting example, in Birkenmeyer et al., J. Clin. Micro. 30: 3089–3094, (1992) and in co-pending application U.S. Ser. No. 722,798, filed Jun. 28, 1991, LCR with a Pilin-2 derived LCR probe set (SEQ ID NOS. 10–13) was described (see Table 3).

TABLE 3

| Position Designation | SEQUENCE and ORIENTATION | SEQ ID No. |
|---|---|---|
| 933.1: | 5'-F1-CGGGCGGGGTCGTCCGTTCC | 10 |
| 933.3: | TGGAAATAATATATCGATT-Bio-3' | 11 |
| 933.2: | 3'-F1-GCCCGCCCCAGCAGGCAA | 12 |
| 933.4: | CCACCTTTATTATATAGCTAA-Bio-5' | 13 |
| Pn2 | GGCCACCTTTATTATATAGCTA-5' | 2 |

This LCR set encompasses sequences of the pilin-coding region from bases 933 to 973, inclusive of and just adjacent to primer Pn 2 (Seq ID NO. 2) described herein, and shown in Table 3 for comparison. It is observed that probe 933.4 (SEQ ID NO. 13) differs from primer Pn2 (SEQ ID NO. 2) in that two Gs are omitted at its 3' end to create the "gap" for gap filling LCR. The 933 probe set was haptenated with biotin or fluorescein as indicated and was used in a gap-filling LCR reaction as published by Birkenmeyer, et al. supra. Targets, along with the range and mean IMx signal-to-noise (S/N) ratios are given in Table 4, below. Target DNA was present as the equivalent of $2.7 \times 10^2$ cells for N. gonorrhoeae, or 3 ng DNA (equivalent to about $1.3 \times 10^6$ cells) for all other species in each reaction.

TABLE 4

| Organism | No. tested | S/N Range | S/N Mean |
|---|---|---|---|
| N. gonorrhoeae; | 136 | 25.0–97.0 | 51.47 |
| N. meningitidis; | 41 | 0.9–1.4 | 1.04 |
| N. lactamica | 10 | 0.9–1.1 | 0.99 |
| Neisseria species[a] | 26 | 0.9–1.2 | 0.98 |
| Non-Neisseria species[b] | 47 | 0.8–1.4 | 1.07 |

[a]Neisseria species included N. subflava (seven strains), N. sicca (six strains), N. cinerea (three strains), N. elongata (two strains), N. flavescens (two strains), N. polysaccharea (two strains), and one strain each of N. flava, N. mucosa, N. perflava, and Neisseria strain ATCC 43831.

TABLE 4-continued

| Organism | No. tested | S/N Range | S/N Mean |
|---|---|---|---|

[b]Non-Neisseria species included bacteria from the following genera: Aeromonas, Acinetobacter (three strains), Alcaligenes, Bacillus, B. catarrhalis. (seven strains), Corynebacter (four strains), Escherichia (two strains), Enterobacter, Gardnerella, Haemophilus (three strains), Herella, Klebsiella, Lactobacillus, Mima, Morax., Proteus (two strains), Providencia, Pseudomonas, Salmonella (two strains), Serratia, Shigella, Staphylococcus (two strains), Streptococcus (two strains), Trichomonas, Veillonella (two strains) and Yersinia.

Results of these assays revealed that the Pilin-2 derived oligonucleotide probes were specific in LCR for N. gonorrhoeae and gave no signal when target DNA from other Neisseria species and Non-Neisseria species were used.

EXAMPLE 5

Detection of Target DNA from N. gonorrhoeae Using Primer Set 13 and PCR

It will be noted that probes 933.1 and 933.4 (SEQ ID NOS. 10 and 13, see Table 3) are properly oriented for performing a modified PCR reaction wherein the 3' ends of each primer terminate at the same position, i.e. the extension product of one primer serves only to orient the opposite primer, but not as a template to direct synthesis of the second extension product. This has been referred to as a "short" PCR product and is particularly useful when the sample DNA is highly fragmented. These probes are used for PCR under conditions as in Example 1 to produce a 41 base pair amplification product.

EXAMPLE 6

Detection of Target DNA from N. gonorrhoeae Using Nucleic Acid Hybridization The oligonucleotides of the present invention may also be used as probes to detect target DNA from N. gonorrhoeae using standard nucleic acid hybridization techniques such as southern blot hybridization, slot blots, dot blots and the like, according to methods well known in the art and as described in Sambrook, J. et al, Molecular Cloning: A Laboratory Manual. Cold Spring Harbor Laboratory Press (1989).

The forgoing examples are presented by way of illustration and are not intended to limit the scope of the invention as set forth in the appended claims. For example, sequences of specific length are listed. It should be understood that sequences covering the same map positions but having slightly fewer or greater numbers are deemed to be equivalents of these sequences and full within the scope of the invention, provided they will hybridize to the same positions on the target as the listed sequences.

We claim:

1. A composition useful in the detection of target DNA from *N. gonorrhoeae*, said composition comprising primer set 1 (SEQ ID NOS. 2 and 3).

2. A method for detecting the presence of target DNA from *N. gonorrhoeae* said method utilizing the polymerase chain reaction and comprising the steps of;
   a) providing a mixture of a sample suspected of containing said target DNA, an enzyme having DNA polymerase activity, and one or more deoxynucleotide triphosphates;
   b) denaturing any double stranded DNA in the mixture;
   c) hybridizing the oligonucleotide primer set of claim 1 to denatured target DNA in said sample;
   d) extending said primers in a template-dependent manner thereby providing an amplification product;
   e) repeating steps b) through d) at least once, whereby DNA of *N. gonorrhoeae* is amplified; and
   f) detecting said amplification product as a measure of the presence of *N. gonorrhoeae*.

3. The method of claim 2 wherein said enzyme is heat stable.

4. The method of claim 3 wherein said heat stable enzyme is derived from a thermophilic Thermus species bacterium.

5. The method of claim 2 Wherein steps b) through d) are repeated 10 to 50 times.

6. The method of claim 2 wherein said amplification products are detected by hybridization to an internal probe complementary to one strand of the amplification products.

7. The method of claim 6 wherein said internal probe has a label capable of generating a signal.

8. The method of claim 2 wherein at least one primer of said primer pair is bound to a specific binding ligand, and wherein step f) includes capture of said ligand on a solid phase by a receptor for said ligand.

9. The method of claim 2 wherein at least one primer of said primer pair is bound to a specific binding ligand, and wherein step f) includes attaching a detectable label to said ligand using a receptor for said ligand conjugated to the detectable label.

10. A kit useful in the specific detection of target DNA from *N. gonorrhoeae* said kit comprising one or more suitable containers containing:

a) primer set 1 (SEQ ID NOS. 2 and 3);

b) an enzyme having DNA polymerase activity, and c) four deoxynucleotide triphosphates.

11. The kit according to claim 10 further comprising an internal probe capable of hybridization to the amplification product produced by the primer pair of claim 10.

12. The kit according to claim 11 wherein said internal probe is an oligonucleotide having 43 bases (SEQ ID NO. 8) as defined herein.

13. The kit according to claim 10 wherein said enzyme is a heat stable DNA polymerase.

14. The kit according to claim 13 wherein said heat stable DNA polymerase is derived from a thermophilic Thermus species bacterium.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:1:

CCAGCTGAGG CAAATTAGG                                                      19

( 2 ) INFORMATION FOR SEQ ID NO:2:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

ATCGATATAT TATTTCCACC GG                                                  22

( 2 ) INFORMATION FOR SEQ ID NO:3:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:3:

CCAAATGAGG CAAATTAGG                                                      19

( 2 ) INFORMATION FOR SEQ ID NO:4:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:4:

ATCAACCCGG GCGGCTTGTC                                                     20

( 2 ) INFORMATION FOR SEQ ID NO:5:

( i ) SEQUENCE CHARACTERISTICS:
      ( A ) LENGTH: 18 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:5:

GAACGGACGA CCCCGCCC                                                                                          18

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CGGGCGGCTT GTC                                                                                               13

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ACGACCCCGC CC                                                                                                12

(2) INFORMATION FOR SEQ ID NO:8:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GATCAACCCG GGCGGCTTGT CTTTTAAGGG TTTGCAAGGC GGG                                                               43

(2) INFORMATION FOR SEQ ID NO:9:

(i) SEQUENCE CHARACTERISTICS:
        (A) LENGTH: 146 base pairs
        (B) TYPE: nucleic acid
        (C) STRANDEDNESS: double
        (D) TOPOLOGY: linear (ii) MOLECULE TYPE: genomic DNA (viii) POSITION IN GENOME:
        (B) MAP POSITION: 827-972

(x) PUBLICATION INFORMATION:
        (A) AUTHORS: T.F. Meyer, E. Billyard, R. Haas, S. Storzbach
            and M. So
        (B) TITLE: Pilus genes of *Neiseria gonorrheae*: Chromosomal
            Organization and DNA Sequence
        (C) JOURNAL: Proc. Natl. Acad. Sci. U.S.A.
        (D) VOLUME: 81
        (F) PAGES: 6110-6114
        (G) DATE: 1984

(xi) SEQUENCE DESCRIPTION: SEQ ID NO:9:

CCAAATGAGG CAAATTAGGC CTTAAATTTT AAATAAATCA AGCGGTAAGT GATTTTCCAC                                             60

CCGCCCGGAT CAACCCGGGC GGCTTGTCTT TTAAGGGTTT GCAAGGCGGG CGGGGTCGTC                                             120

CGTTCCGGTG GAAATAATAT ATCGAT                                                                                 146

( 2 ) INFORMATION FOR SEQ ID NO:10:

( i ) SEQUENCE CHARACTERISTICS:
     ( A ) LENGTH: 20 base pairs
     ( B ) TYPE: nucleic acid
     ( C ) STRANDEDNESS: single
     ( D ) TOPOLOGY: linear ( i i ) MOLECULE TYPE: DNA ( x i ) SEQUENCE DESCRIPTION: SEQ ID NO:10:

CGGGCGGGGT CGTCCGTTCC 20

( 2 ) INFORMATION FOR SEQ ID NO:11:

( i ) SEQUENCE CHARACTERISTICS:
     ( A ) LENGTH: 19 base pairs
     ( B ) TYPE: nucleic acid
     ( C ) STRANDEDNESS: single
     ( D ) TOPOLOGY: linear ( i i ) MOLECULE TYPE: DNA ( x i ) SEQUENCE DESCRIPTION: SEQ ID NO:11:

TGGAAATAAT ATATCGATT 19

( 2 ) INFORMATION FOR SEQ ID NO:12:

( i ) SEQUENCE CHARACTERISTICS:
     ( A ) LENGTH: 18 base pairs
     ( B ) TYPE: nucleic acid
     ( C ) STRANDEDNESS: single
     ( D ) TOPOLOGY: linear ( i i ) MOLECULE TYPE: DNA ( x i ) SEQUENCE DESCRIPTION: SEQ ID NO:12:

AACGGACGAC CCCGCCCG 18

( 2 ) INFORMATION FOR SEQ ID NO:13:

( i ) SEQUENCE CHARACTERISTICS:
     ( A ) LENGTH: 21 base pairs
     ( B ) TYPE: nucleic acid
     ( C ) STRANDEDNESS: single
     ( D ) TOPOLOGY: linear ( i i ) MOLECULE TYPE: DNA ( x i ) SEQUENCE DESCRIPTION: SEQ ID NO:13:

AATCGATATA TTATTTCCAC C 21